(12) United States Patent
Cutler

(10) Patent No.: US 8,658,139 B1
(45) Date of Patent: Feb. 25, 2014

(54) PREVENTION AND TREATMENT OF ORAL DISEASES

(75) Inventor: Edward T. Cutler, Narberth, PA (US)

(73) Assignee: Squigle, Inc., Narberth, PA (US)

( * ) Notice: Subject to any disclaimer, the term of this patent is extended or adjusted under 35 U.S.C. 154(b) by 686 days.

(21) Appl. No.: 12/660,485

(22) Filed: Feb. 27, 2010

(51) Int. Cl.
*A61Q 11/00* (2006.01)
*A61K 8/00* (2006.01)
*A61K 33/06* (2006.01)

(52) U.S. Cl.
USPC .............................. 424/49; 424/401

(58) Field of Classification Search
USPC .................. 424/49, 401; 433/216, 217.1
See application file for complete search history.

(56) References Cited

U.S. PATENT DOCUMENTS

| | | | |
|---|---|---|---|
| 4,634,589 A | 1/1987 | Scheller | |
| 4,645,662 A | 2/1987 | Nakashima et al. | |
| 4,988,499 A | 1/1991 | Bristow et al. | |
| 4,992,258 A | 2/1991 | Mason | |
| 5,135,396 A | 8/1992 | Kuboki | |
| 5,244,651 A | 9/1993 | Kayane et al. | |
| 5,496,541 A * | 3/1996 | Cutler | 424/49 |
| 5,589,159 A | 12/1996 | Markowitz et al. | |
| 5,597,552 A | 1/1997 | Herms et al. | |
| 5,605,675 A | 2/1997 | Usen et al. | |
| 5,624,906 A * | 4/1997 | Vermeer | 514/23 |
| 5,693,314 A | 12/1997 | Campbell et al. | |
| 5,718,885 A | 2/1998 | Gingold et al. | |
| 5,762,911 A | 6/1998 | Kleinberg et al. | |
| 5,766,011 A | 6/1998 | Sibner | |
| 5,833,959 A | 11/1998 | Atsumi et al. | |
| 5,843,409 A | 12/1998 | Campbell et al. | |
| 5,874,066 A | 2/1999 | Hack et al. | |
| 5,900,230 A | 5/1999 | Cutler | |
| 5,906,809 A | 5/1999 | Hack et al. | |
| 5,981,475 A | 11/1999 | Reynolds | |
| 6,180,089 B1 | 1/2001 | Gambogi et al. | |
| 6,241,972 B1 | 6/2001 | Herms et al. | |
| 6,338,751 B1 | 1/2002 | Litkowski et al. | |
| 6,416,745 B1 | 7/2002 | Markowitz et al. | |
| 6,436,370 B1 | 8/2002 | Kleinberg et al. | |
| 6,447,756 B1 | 9/2002 | Dixit et al. | |
| 6,524,558 B2 | 2/2003 | Kleinberg et al. | |
| 6,953,817 B2 | 10/2005 | Fisher et al. | |
| 7,182,937 B2 | 2/2007 | Xu et al. | |
| 2001/0044096 A1 | 11/2001 | Lindquist | |
| 2002/0037258 A1 | 3/2002 | Dodd et al. | |
| 2002/0041852 A1 | 4/2002 | Napolitano et al. | |
| 2003/0133885 A1 | 7/2003 | Kleinberg et al. | |
| 2003/0215401 A1 | 11/2003 | Estrada et al. | |
| 2004/0022746 A1 | 2/2004 | Fisher et al. | |
| 2004/0022747 A1 | 2/2004 | Fisher et al. | |
| 2004/0086467 A1 | 5/2004 | Curro | |
| 2004/0185027 A1 | 9/2004 | Reierson et al. | |
| 2006/0193792 A1* | 8/2006 | Corcoran et al. | 424/49 |
| 2007/0059257 A1 | 3/2007 | Estrada et al. | |
| 2007/0196287 A1 | 8/2007 | Fischer | |

FOREIGN PATENT DOCUMENTS

| | | |
|---|---|---|
| CN | 1348757 | 5/2002 |
| EP | 0346957 | 12/1989 |
| EP | 0721773 | 7/1996 |
| JP | 60184007 | 9/1985 |
| JP | 6-122616 | 5/1994 |
| JP | 9-175963 | 7/1997 |
| JP | 9-235215 | 9/1997 |
| JP | 9-295924 | 11/1997 |
| JP | 10-059814 | 3/1998 |
| JP | 10-109915 | 4/1998 |
| JP | 10-330234 | 12/1998 |
| JP | 11-35438 | 2/1999 |
| JP | 11-130643 | 5/1999 |
| JP | 2001-213746 | 8/2001 |
| JP | 2008-007479 | 1/2008 |
| WO | WO 99/20237 | 4/1999 |

OTHER PUBLICATIONS

Medline Plus, Dental Caries, pp. 1-3, May 2001.*
Absi et al, Dentine Hypersensitivity: uptake of toothpastes onto dentine and effects of brushing, washing and dietary acid—SEM in vitro study, J. Oral Rehabilitation, Mar. 1995, 22, 175.
Addy, P. Mostafa, "Dentine hypersensitivity. II. Effects produced by the uptake in vitro of toothpastes onto dentine", J. Oral Rehabilitation, Jan. 1989, 16(1), 35-48.
Addy et al., "Dentine hypersensitivity: a comparison of five toothpastes used during a 6-week treatment period", Brit. Dent. J., Jul. 1987,163, 45-51.
Arrais, et al., "Occluding effect of dentifrices on dentinal tubules", Journal of Dentistry, Nov. 2003, 31(8), 577-584.
Assev et al., Are sodium lauryl sulfate-Containing toothpastes suitable vehicles for xylitol? European Journal of Oral Sciences, Apr. 1997, 105(2), 178-182.
Assev, S. and G. Rölla, Lack of xylitol uptake by bacteria in the presence of SLS, Caries Res., 1995, 29, 297.
Barone, M. and M. Malpissi, "Clinical Trial of a 15% supermicronized hydroxyapatite gel for dentin hypersensitivity, Giornale Italiano di Endodonzia", 1991, 5 (2), 43-47.
Cutler et al, "Gum Disease Clinical Study 1999-2000", The Effect of toothpaste on bleeding index, 2000, 1-3.

(Continued)

*Primary Examiner* — Lezah Roberts

(57) ABSTRACT

This invention comprises a set of dental products and methods to prevent and treat dentinal hypersensitivity, prevent tooth decay, and heal incipient caries by means of Mouth Friendly® dental products containing calcium carbonate, having a preferred particle size of 1 to 100 nanometers (nm), and a preferred weight range of 5 to 30%. Said products must contain 8 to 95 weight percent of xylitol, plus the surfactant system described in U.S. Pat. No. 5,496,541 (Mar. 5, 1996) and U.S. Pat. No. 5,900,230 (May 4, 1999). It is further required that all irritants and other mouth unfriendly ingredients be absent from the dental products of this invention. Additional features of this invention include prevention and treatment of aphthous ulcers, oral mucositis, periodontal disease, perioral dermatitis, halitosis, oral candida, chapped lips, and oral plaque and tartar. This invention also ameliorates the condition of those who suffer from xerostomia and cold sores.

23 Claims, No Drawings

(56) References Cited

OTHER PUBLICATIONS

Forssell-Ahlberg, "The diameter and number of dentinal tubules in rat, cat, dog and monkey", Acta Odon. Scand., 1975, 33(5), 243-250.

Gillam et al., "Clinical efficacy of a low abrasive dentifrice for the relief of cervical dentinal hypersensitivity", J. Clin. Periodontol., Mar. 1992, 19(3), 197-201.

Gillam et al., "Dentifrice abrasivity and cervical dentinal hypersensitivity. Results 12 weeks following cessation of 8 weeks' supervised use", Jan. 1992, J. Periodontol., 63(1), 7.

Hüttemann et al. Investigation of utility and mechanics of use of hydroxyapatite for therapy of hypersensitive tooth root, ZWR, Mar. 1989, 98 (3), 240-245.

Hüttemann, R. and H. Donges, "Treatment of dentine hypersensitivity with hydroxylapatite", Dtsch. Zahnärztl. Z., May 1987, 42(5), 486-488.

Kuroiwa et al., Dentin hypersensitivity. Occlusion of dentinal tubules by brushing with and without an abrasive dentifrice, J. Periodontol., Apr. 1994, 65, 291-296.

Melsen, B., and G. Rölla, "Reduced clinical effect of monofluorophosphate in the presence of sodium lauryl sulphate", Caries Res., 1983, 17(6), 549-553.

Nakashima et al, "Effect of a Test Dentifrice Containing Nano-sized Calcium Carbonate on Remineralization of Enamel Lesions in Vitro", Mar. 2009, Journal of Oral Science, 51(1), 69-77.

Prati et al., "Dentin morphology and permeability after brushing with different toothpastes in the presence and absence of smear layer", J. Periodontol., Feb. 2002, 73(2), 183-190.

West et al., "Dentine hypersensitivity: the effects of brushing toothpaste on etched and unetched dentine in vitro", Feb. 2002, J. Oral Rehabilitation, 29(2), 167-174.

\* cited by examiner

PREVENTION AND TREATMENT OF ORAL DISEASES

This invention comprises a set of dental products and methods to prevent and treat dentinal hypersensitivity, prevent tooth decay, and heal incipient caries by means of Mouth Friendly® dental products containing calcium carbonate, having a preferred particle size of 1 to 100 nanometers (nm), and a preferred weight range of 5 to 30%. Said products must contain 8 to 95 weight percent of xylitol, plus the surfactant system described in U.S. Pat. No. 5,496,541 (Mar. 5, 1996) and U.S. Pat. No. 5,900,230 (May 4, 1999). It is further required that all irritants and other mouth unfriendly ingredients be absent from the dental products of this invention. Additional features of this invention include prevention and treatment of aphthous ulcers, oral mucositis, periodontal disease, perioral dermatitis, halitosis, oral candida, chapped lips, and oral plaque and tartar. This invention also ameliorates the condition of those who suffer from xerostomia and cold sores.

BACKGROUND OF THE INVENTION 15 to 20% of the population suffer from dentinal hypersensitivity, also known as tooth sensitivity. This malady is characterized by pain associated with ingestion of hot or cold foods, or sweets, or salty food, or pressure from toothbrushing. It is due to open dentinal tubules, usually near the gum line.

Tooth sensitivity is mainly caused by:
- corrosion of enamel by acidic food and beverages
- overzealous toothbrushing
- excessively abrasive toothpastes
- use of ultra abrasive prophylaxis pastes when you get your teeth cleaned at the dentist
- gastric reflux—voluntary or involuntary
- gum recession
- bruxism Until recently, most treatments were palliative, and involved using toothpaste containing potassium salts, in particular 5% by weight of potassium nitrate in the US. Potassium cation raises the firing threshold of pulpal nerves.

A better approach is to use a dentinal tubule occluding agent. It is known that the average diameter of dentinal tubules in humans is about 1 micrometer ($1\mu$). See: K. Forssell-Ahlberg et al., *Acta Odon. Scand.*, 33, 243 (1975). In order for a particle to enter and occlude a dentinal tubule, it must have a diameter less than said tubule. Most prior art does not tabulate or graph the particle size distribution of the dentinal tubule occluding particles under consideration. Absent such information, when a particle size is mentioned, the reader should assume what is meant is average particle size.

In January, 1998 a new toothpaste, SQUIGLE® Enamel Saver® (made by SQUIGLE, inc., Narberth, Pa.) came on the market in the US. This toothpaste contains 36 weight percent of xylitol plus the surfactant system described in U.S. Pat. No. 5,496,541 (Mar. 5, 1996). Said toothpaste is free of irritating ingredients and was intended to help prevent oral maladies such as canker sores and cavities. But it was also found to treat and prevent periodontal disease (U.S. Pat. No. 5,900,230 May 4, 1999). A double blind clinical trial conducted by the US Army at Fort Sam Houston, Tex. (1999 to 2000, unpublished) confirmed the clinical efficacy of SQUIGLE® Toothpaste in the treatment and prevention of periodontal disease.

Quite unexpectedly, SQUIGLE® Enamel Saver® Toothpaste was also found to eliminate dentinal hypersensitivity in about half of all users who had this condition and used SQUIGLE® Toothpaste regularly. Since SQUIGLE® has no local anesthetics, such as potassium nitrate and/or other soluble potassium salts, its efficacy must be due to the finely divided solids present therein, such as the submicron portion of the abrasive silica and the colorant titanium dioxide, acting as dentinal tubule occluding agents, aided by the 36% xylitol and the surfactant system used in said toothpaste. For comparison, conventional toothpaste, which frequently has the same abrasive silica (average particle size=8 to $15\mu$) and colorant titanium dioxide (average particle size=$1\mu$) as SQUIGLE®, does not have the ability to occlude open dentinal tubules the way SQUIGLE® Toothpaste does.

The tubule occluding effect of amorphous silica in toothpaste has been known for some time but, until now, the details and optimal formulations have been lacking. See:

M. Addy et al., *Brit. Dent. J.*, 163, 45 (1987)
M. Addy, P. Mostafa, *J. Oral Rehabilitation*, 16, 35 (1989)
D. Gillam et al., *J. Clin. Periodontol.*, 19, 197 (1992)
D. Gillam et al., *J. Periodontol.*, 63, 7 (1992)
M. Kuroiwa et al., *J. Periodontol.*, 65, 291 (1994)
E. Absi et al., *J. Oral Rehabilitation*, 22, 175 (1995)
C. Prati et al., *J. Periodontol.*, 73, 183 (2002)
N. West et al., *J. Oral Rehabilitation*, 29, 167 (2002)

PRIOR ART

Products Involving Crystalline Calcium Phosphate

Over 70 years ago, Ecodent Toothpowder, the first amorphous calcium phosphate dentifrice, appeared. This product, still sold today, consists of granules containing (among other things) $CaCO_3 + CaHPO_4 +$ tartaric acid. Said granules generate amorphous calcium phosphate when contacted with water.

In 1987, R. Hüttemann and H. Dönges, published an article [*Dtsch. Zahnärztl. Z.*, 42, 486 (1987)] which stated that a toothpaste containing 17% by weight of hydroxyapatite (HAP) having a particle size of $2\mu$ very effectively reduced or eliminated dentinal hypersensitivity. In 1989 R. Hütteman et al. [*ZWR*, 98 (3), 240 (1989)] revealed that said toothpaste was Oral B Sensitive, a commercial product that has been on the market since the mid 1980s. It is known that a signficant number of HAP particles in Oral B Sensitive have a size equal to or less than $1\mu$. In 1991 M. Barone and M. Malpissi published an article [*Giornale Italiano di Endodonzia*, 5 (2), 43 (1991)] wherein they discussed a toothpaste (Apagen, commercially available) which contained submicron sized HAP particles to treat dentinal hypersensitivity.

HAP toothpastes, containing micro- and nanocrystals of HAP include Apagen Toothpaste (made in Italy), Apagard Toothpaste (made in Japan), and Oral-B Sensitive (made in the Netherlands).

Table 1 provides a list of patents which describe crystalline HAP products used to treat dentinal hypersensitivity.

TABLE 1

| Crystalline Hydroxyapaptite (HAP) Products used to treat Dentinal Hypersensitivity | |
|---|---|
| Application or Pat. No. | Publication or Issue Date |
| U.S. Pat. No. 4,634,589 | Jan. 6, 1987 |
| EP 346,957 | Dec. 5, 1989 |
| U.S. Pat. No. 4,988,499 | Jan. 29, 1991 |
| U.S. Pat. No. 5,135,396 | Aug. 4, 1992 |
| JP 6-122,616 | May 6, 1994 |
| JP 9-175,963 | Jul. 8, 1997 |

TABLE 1-continued

Crystalline Hydroxyapaptite (HAP) Products
used to treat Dentinal Hypersensitivity

| Application or Pat. No. | Publication or Issue Date |
|---|---|
| JP 9-235,215 | Sep. 9, 1997 |
| JP 10-59,814 | Mar. 3, 1998 |
| JP 10-109,915 | Apr. 28, 1998 |
| U.S. Pat. No. 5,833,959 | Nov. 10, 1998 |
| JP 10-330,234 | Dec. 15, 1998 |
| WO 99/20237 | Apr. 29, 1999 |
| JP 2001-213,746 | Aug. 7, 2001 |

Nanotoxicity—The Shape Problem

One problem with crystalline hydroxyapatite is its acicular shape. Much effort has been expended in attempts to modify the natural shape of hydroxyapatite, in order to make it less needle like, and thus less toxic to mammalian cells. A similar problem exists with silica, which can exist in both the acicular and spheroidal shape. It is relatively easy to make amorphous (spheroidal) silica; however, amorphous silica is not metabolized by mammalian cells. Calcite does not have a shape problem—it is naturally cuboidal, and it is easily metabolized by mammalian cells.

PRIOR ART

Products Involving Amorphous Calcium Phosphate

Recently, amorphous calcium phosphate toothpastes have appeared, which form amorphous calcium phosphate in situ via
a. Mixing solutions of $Ca^{+2}$ and $(PO_4)^{-3}$
  (see U.S. Pat. No. 5,605,675 Feb. 25, 1997)
b. Mixing finely divided sodium calcium phosphosilicate glass with saliva
  (see U.S. Pat. No. 6,338,751 Jan. 15, 2002)
c. Coating teeth with calcium phosphopeptides
  (see U.S. Pat. No. 5,981,475 Nov. 9, 1999)
d. Brushing with an anhydrous toothpaste containing {water soluble calcium salts} and {water soluble phosphates or silicates} (see U.S. Pat. No. 7,182,937 Feb. 27, 2007)

PRIOR ART

Products Involving Calcium Carbonate

In 1997, Lion Corporation published a patent [JP9-295924 (Nov. 18, 1997)] which discusses the ability of submicron sized calcite to neutralize plaque acids and thereby prevent caries in hamsters. This submicron sized calcite adheres to the hard and soft tissues of the mouth and to plaque and tartar, and reacts with acids as they appear anywhere in the mouth. There are 8 examples of toothpaste, and all but Example 2 list sodium monofluorophosphate (NaMFP) or NaF as an ingredient. Example 2 lists cetylpyridinium chloride (0.3% by weight) instead of fluoride. Examples 3 and 7 list xylitol (20% by weight) as a dentifrice ingredient. All 8 toothpastes list SLS as an ingredient. JP9-295924 does not demonstrate awareness of the adverse effect of SLS on the antiplaque efficacy of xylitol. However, said adverse effect is discussed in the following papers:
S. Assev, G. Rölla, Caries Res., 29, 297 (1995).
S. Assev et al., Eur. J. Oral Sci., 105, 178 (1997).

According to JP9-295924 (paragraph 22), nanocalcite can be blended with thickeners, including, among others, cellulose gum and/or hydroxyethyl cellulose and/or poloxamer. But the surfactant system of U.S. Pat. No. 5,900,230 and U.S. Pat. No. 5,496,541 is not mentioned. And JP9-295924 does not mention the effect of submicron sized calcite on dentinal hypersensitivity.

JP11-35438 (Feb. 9, 1999) discusses dental products containing nanocalcite plus dextranase plus anionic detergents such as sodium N-lauroyl sarcosinate and sodium lauryl sulfate. In contrast, the dental products of my invention explicitly avoid use of anionic detergents, and dextranase is not mentioned.

According to JP11-35438 (paragraph 19), nanocalcite can be blended with thickeners including, among others, cellulose gum and/or hydroxyethyl cellulose. Pluronic is mentioned, among others, as a detergent (paragraph 19). But the surfactant system of U.S. Pat. No. 5,900,230 and U.S. Pat. No. 5,496,541 is not mentioned. Xylitol is never mentioned. And the effect of nanocalcite on dentinal hypersensitivity is not mentioned.

JP11-130643 (May 18, 1999) discusses dental products containing colloidal calcite (particle size=3μ or less) plus NaF or NaMFP. JP11-130643 claims that the adherence of fluoridated nanocalcite in the mouth, and its subsequent dissolution, makes the fluoride, originally from NaMFP and NaF, bioavailable. In contrast, NaF is quickly inactivated, and washed out of the mouth, when micron sized calcite is used as an abrasive.

According to JP11-130643 (paragraph 19), colloidal calcite can be blended with thickeners including, among others, cellulose gum and/or hydroxyethyl cellulose and/or poloxamer. But the surfactant system of U.S. Pat. No. 5,900,230 and U.S. Pat. No. 5,496,541 is not mentioned. Xylitol is mentioned as a humectant, among others (paragraph 21), but its antiplaque properties are not mentioned. And the effect of nanocalcite on dentinal hypersensitivity is not mentioned.

JP2008-7479 (Jan. 17, 2008) discusses dental products to combat caries, gum disease, and halitosis. Said products contain slightly water soluble medicinals (paragraph 18), such as triclosan, surrounded by a nanocalcite layer, in an aqueous sugar alcohol suspending liquid. Xylitol and sorbitol are the preferred sugar alcohols (paragraph 60). But the antiplaque properties of xylitol are not mentioned, and simple nanocalcite particles are not discussed.

The dental products according to JP2008-7479 (paragraph 58) may contain thickeners including, among others, cellulose gum and/or hydroxyethyl cellulose. Pluronic is mentioned, among others, as a nonionic detergent (paragraph 59). But the surfactant system of U.S. Pat. No. 5,900,230 and U.S. Pat. No. 5,496,541 is not mentioned. And the effect of nanocalcite on dentinal hypersensitivity is not mentioned.

Recently, an article about a "test dentifrice" containing nanocalcite (size=several 10 s to 100 s of nm) has appeared [S. Nakashima et al., J. Oral Sci., 51 (1), 69 (2009)]. This article, written by workers at Lion Corporation, describes their initial studies of a toothpaste containing 1% by weight of nanocalcite and its ability to remineralize enamel lesions (white spots) in vitro. This toothpaste contains the severe mouth irritant sodium lauryl sulfate (SLS), which Nakashima et al. acknowledge has an adverse influence on the anticaries action of NaMFP [see: B. Melsen, G. Rölla, Caries Res., 17, 549 (1983)]. S. Nakashima et al. do not mention the effect of nanocalcite on dentinal hypersensitivity. Nor do they mention the profound plaque suppressor, xylitol.

Although the "test dentifrice" contains 0.76% NaMFP, Nakashima et al. suggest that the remineralizing ability of said dentifrice "could be ascribed solely to the presence of nanocalcite, which releases calcium ions, and probably OH⁻ ions".

Recently, a toothpaste and a prophylaxis paste containing calcium carbonate together with L-arginine bicarbonate have appeared [see U.S. Pat. No. 5,762,911 (Jun. 9, 1998), U.S. Pat. No. 6,436,370 (Aug. 20, 2002), U.S. Pat. No. 6,524,558 (Feb. 25, 2003), and US Application 2003/0133885 (Jul. 17, 2003)]. These patents do not mention submicron sized calcite. And the surfactant system of U.S. Pat. No. 5,900,230 and U.S. Pat. No. 5,496,541 is not mentioned.

The tubule occluding effect of calcium carbonate in toothpaste has been known for some time but, until now, the details and optimal formulations have been lacking. See: C. Arrais, et al., *J. Dentistry*, 31, 577 (2003)

PRIOR ART

Miscellaneous Products

In addition to the products listed above to treat dentinal hypersensitivity, there are miscellaneous products, such as those listed in Table 2.

TABLE 2

Miscellaneous products used to Treat Dentinal Hypersensitivity

| Application or Pat. No. | Publication or Issue Date | Description |
| --- | --- | --- |
| EP 0721773 | Jul. 17, 1996 | Ca-polymer emulsions + oxalic acid |
| JP 60184007 | Sep. 19, 1985 | Al chlorohydroxide-propylene glycol |
| U.S. Pat. No. 4,645,662 | Feb. 24, 1987 | Al carboxylate |
| U.S. Pat. No. 4,992,258 | Feb. 12, 1991 | montmorillonite clay + polymeric polycarboxylate |
| U.S. Pat. No. 5,244,651 | Sep. 14, 1993 | colloidal metal polyol phosphates |
| U.S. Pat. No. 5,589,159 | Dec. 31, 1996 | laponite clay |
| U.S. Pat. No. 5,597,552 | Jan. 28, 1997 | polyacrylic acid salts |
| U.S. Pat. No. 5,693,314 | Dec. 2, 1997 | $SnF_2$ and $KNO_3$ |
| U.S. Pat. No. 5,718,885 | Feb. 17, 1998 | cationically charged metal colloids |
| U.S. Pat. No. 5,766,011 | Jun. 16, 1998 | pH 9.5 + NaF |
| U.S. Pat. No. 5,843,409 | Dec. 1, 1998 | $SnF_2$ and $KNO_3$ |
| U.S. Pat. No. 5,874,066 | Feb. 23, 1999 | $SrCl_2$ or $CaCl_2$ + K oxalate |
| U.S. Pat. No. 5,906,809 | May 25, 1999 | $SrCl_2$ or $CaCl_2$ + K oxalate |
| U.S. Pat. No. 6,180,089 | Jan. 30, 2001 | NaF and $KNO_3$ |
| U.S. Pat. No. 6,241,972 | Jun. 5, 2001 | polymeric polycarboxylic acid salts |
| U.S. Pat. No. 6,416,745 | Jul. 9, 2002 | anionic liposomes |
| U.S. Pat. No. 6,447,756 | Sep. 10, 2002 | Na silicate + $KNO_3$ |
| U.S. Pat. No. 6,953,817 | Oct. 11, 2005 | $SnF_2$ and $KNO_3$ |
| US 2001/0044096 | Nov. 22, 2001 | acceleration of desensitization by heating |
| US 2002/0037258 | Mar. 28, 2002 | calcium silicate mixtures |
| US 2002/0041852 | Apr. 11, 2002 | organic polymer tubule occluders |
| US 2003/0215401 | Nov. 20, 2003 | organic polymer tubule occluders |
| US 2004/0022746 | Feb. 5, 2004 | $SnF_2$ and $KNO_3$ |
| US 2004/0022747 | Feb. 5, 2004 | $SnF_2$ and $KNO_3$ |
| US 2004/0086467 | May 6, 2004 | coated substrates |
| US 2004/0185027 | Sep. 23, 2004 | mono-and dialkylphosphate esters |
| US 2007/0059257 | Mar. 15, 2007 | organic polymer tubule occluders |
| US 2007/0196287 | Aug. 23, 2007 | F⁻ plus a low concentration of $KNO_3$ |

U.S. Pat. No. 5,718,885 (Feb. 17, 1998) discusses cationically charged colloids to treat dentinal hypersensitivity. These colloids comprise metal compounds including groups II A, which includes the metal calcium. However, the preferred metals are Y, Ce, Al, and Zr (claim 4). And the preferred anions are halide, oxide, hydroxide, silicate, or acetate (claim 7). Carbonate is never mentioned as a suitable anion. Thus, the only possible calcium-containing colloid would have to be calcium silicate.

The only time U.S. Pat. No. 5,718,885 mentions colloidal silica, is in the form of alumina-coated silica (Column 4, lines 34 to 39 and Column 6, lines 15 to 26 and Example 25).

US Application 20040086467 (May 6, 2004) discusses a substrate coated with a desensitizing agent. Both silica and calcium carbonate are listed as possible substrates (paragraph 24). And calcium carbonate is listed as a possible desensitizing agent with which to "treat the substrate" (paragraph 20). But the substrate size range is too large—10μ or less (claim 4). Paragraph 24 says the preferred substrate size range is 0.5 to about 2μ, which is still too large, compared to the preferred range of my invention, which is 0.001 to 0.1μ (1 to 100 nm).

SUMMARY OF THE INVENTION

This invention comprises a set of dental products and methods to prevent and treat dentinal hypersensitivity, prevent tooth decay, and heal incipient caries by means of Mouth Friendly® dental products containing calcium carbonate, having a preferred particle size of 1 to 100 nm, and a preferred weight range of 5 to 30%. Said products must contain 8 to 95 weight percent of xylitol, plus the surfactant system described in U.S. Pat. No. 5,496,541 (Mar. 5, 1996) and U.S. Pat. No. 5,900,230 (May 4, 1999). It is further preferred that all irritants and other mouth unfriendly ingredients be absent from the dental products of this invention. Additional features of this invention include prevention and treatment of aphthous ulcers, oral mucositis, periodontal disease, perioral dermatitis, halitosis, oral candida, chapped lips, and oral plaque and tartar. This invention also ameliorates the condition of those who suffer from xerostomia and cold sores.

DETAILED DESCRIPTION OF THE INVENTION AND ITS PREFERRED EMBODIMENTS

This invention encompasses Mouth Friendly® oral care products (including a dentifrice powder, granules, or disintegrable tablets, toothpaste, prophylaxis paste, toothpaste for infants and toddlers, dental lozenge, dental chewing gum, mouthwash, and a dry mouth paste), and the methods of use of said products to prevent and treat dentinal hypersensitivity, prevent tooth decay, and heal incipient caries. Additional features of this invention include prevention and treatment of aphthous ulcers, oral mucositis, periodontal disease, perioral dermatitis, halitosis, oral candida, chapped lips, and oral plaque and tartar. This invention also ameliorates the condition of those who suffer from xerostomia and cold sores.

The oral care products of this invention must contain:

(a) 0.25 to 40 weight percent of calcium carbonate particles having a particle size of 1 to 1000 nm. The preferred weight range is 5 to 30%, and the preferred size range is 1 to 100 nm. For example, one may use Multifex® MM, average particle size=70 nm, made by Specialty Minerals Inc.

(b) 8 to 95 weight percent of xylitol. The preferred weight range is 30 to 40% for toothpaste, dry mouth paste, and mouthwash, and 50 to 90% for the dental powder, granules, tablets, lozenges, and chewing gum of this invention.

(c) the surfactant system described in U.S. Pat. No. 5,496, 541 (Mar. 5, 1996) and U.S. Pat. No. 5,900,230 (May 4, 1999). Each embodiment contains 0.01 to 10% by weight of poloxamer, or a mixture of poloxamers, plus an anionic polysaccharide (AP), or a mixture of APs, plus a nonionic cellulose ether (NCE), or a mixture of NCEs, in a ternary surfactant system having enhanced foaming power relative to poloxamers alone or to poloxamers plus APs or to poloxamers plus NCEs, wherein the weight ratio of said poloxamer to said APs is greater than 1, and the weight ratio of said AP to said NCE is greater than 1.

Poloxamers are block copolymers of ethylene oxide and propylene oxide arranged as $(EO)_a(PO)_b(EO)_a$ wherein the PO content ranges from 15 to 85 mole percent, and the molecular weight ranges from 1,000 to 30,000.

The APs are selected from the group consisting of alginic acid, gum arabic, carrageenan, carboxymethyl cellulose, karaya gum, pectin, gum tragacanth, and xanthan gum. High molecular weight polyacrylic acids (PAAs), linear or crosslinked, can fully or partially replace the APs of this invention. Said PAAs have a molecular weight range of 700,000 to 5 million.

The NCEs are selected from the group consisting of alkylated celluloses and hydroxyalkylated celluloses, selected from the group consisting of methylcellulose, ethylcellulose, hydroxyethylcellulose, hydroxypropylcellulose, and hydroxypropylmethylcellulose. High molecular weight polyethyleneoxides (PEOs) can fully or partially replace the NCEs of this invention. Said PEOs have a molecular weight range of 100,000 to 8 million The dental products of this invention may also contain one or more optional ingredients:

a. 5 to 90% by weight of polyol humectants selected from the group consisting of glycerol, erythritol, sorbitol, mannitol, maltitol, and polyethylene glycol.

b. 0.001 to 5% by weight of sweeteners selected from the group consisting of acesulfame and its salts, aspartame, dihydrochalcones, glycyrrhizin and its derivatives, raw and extracted licorice, saccharin, stevia and the rebaudosides, sucralose, talin and the thaumatins.

c. 1 to 60% by weight of a mild abrasive, having a hardness less than or equal to that of tooth enamel, selected from the group consisting of calcium carbonate, dibasic calcium phosphate, tribasic calcium phosphate, calcium pyrophosphate, and hydroxyapatite d. 1 to 60% by weight of a strong abrasive, having a hardness greater than that of tooth enamel, selected from the group consisting of alumina, silica, titania, and fluoroapatite e. 0.1 to 10% by weight of flavor f. 1 to 5000 ppm by weight of a fluoride containing compound selected from the group consisting of sodium fluoride and sodium monofluorophosphate g. 0.1 to 10% by weight of a mono-, di-, or polydentate acid or its salts selected from the group consisting of citric acid, ethylenediaminetetraacetic acid, ascorbic acid, phosphoric acid, hydrochloric acid, and sulfuric acid to adjust and maintain the pH between 6 and 10 h. 0.1 to 1.0% by weight of preservative selected from the group consisting of paraben, potassium sorbate, lactoferrin, lysozyme, and calcium propionate i. 0.1 to 1.0% by weight of antioxidant selected from the group consisting of ascorbic acid, α-tocopherol, β-carotene, coenzyme $Q_{10}$ and melatonin j. 5 to 95% by weight of water k. 0.1 to 10% of a thickener selected from the group consisting of colloidal cellulose, hydrated silica, polyethylene glycol, and polyvinylpyrrolidone It is preferred that all irritants and mouth unfriendly ingredients be absent from the dental products of this invention. Said dental products being free of irritating detergents, such as sodium lauryl sulfate, sodium N-lauroyl sarcosinate, cocamidopropyl betaine, sodium N-lauroyl glutamate, and sodium methyl cocoyl taurate. Said dental products being free of irritating flavors and essential oils, such as phenol, thymol, carvacrol, clove, spearmint, cinnamon, eucalyptol, and no flavors present at high intensity. Said dental products being free of irritating antimicrobials, such as chlorhexidine, alexidine, cetylpyridinium chloride, benzalkonium chloride, benzethonium chloride, sanguinarine, and triclosan. Said dental products being free of irritating tartar control agents, such as inorganic phosphate salts of group I metals, including metaphosphates, polyphosphates, and pyrophosphates.

It is preferred that the dental products of this invention be free of all surfactants other than those of the surfactant system of poloxamers, {APs and/or PAAs}, and {NCEs and/or PEOs}.

It is preferred that the dental products of this invention be free of foam suppressors, such as sulfonated polyacrylate oligomers, polydimethylsiloxanes, and azacycloalkane-2,2-diphosphonic acids.

The nanocalcite of this invention adheres to the hard and soft tissues of the mouth and to plaque and tartar, instantly absorbing protons and releasing $Ca^{++}$ and $HCO_3^-$ ions whenever and wherever acid is released, thereby providing an instantaneous means to remineralize decalcified enamel. Consider the atmosphere inside your mouth. Exhaled breath is rich in $CO_2$ (4% by volume) versus room air (0.04% by volume). Thus, mouth air can mildly acidify the mouth, which facilitates the slow dissolution of nanocalcite, thereby helping to continuously bathe the mouth in saliva enriched in $Ca^{++}$, which will remineralize the mouth for as many hours as the nanocalcite coating persists in the mouth.

The nanocalcite of this invention migrates into open dentinal tubules, and sticks there, occluding open tubules within 1 to 2 weeks when teeth are brushed with the toothpaste of this invention. And said nanocalcite inhibits the formation of tartar by sequestering phosphate ions.

The xylitol of this invention profoundly inhibits the growth of plaque, thereby facilitating migration of the nanoparticles of this invention into open dentinal tubules. Similarly, xylitol facilitates migration of salivary calcium and phosphate ions into the open dentinal tubules, which helps cement in place the nanoparticles of this invention. And xylitol's profound inhibition of the growth of plaque on the hard and soft tissues of the mouth facilitates the attachment of the nanocalcite particles directly to said tissues. Over time, xylitol transforms oral flora into a more benign (less acidogenic) group. Since xylitol profoundly inhibits the growth of plaque, the amount of calcified plaque (tartar) is reduced, too.

The surfactant system foam of this invention adheres xylitol and the nanoparticles of this invention to the teeth and soft tissues. Said surfactant system also prevents agglomeration of the nanoparticles, and it lubricates the nanoparticles, so as to facilitate their migration into open dentinal tubules. And said surfactant system does not irritate pulpal nerves. During manufacturing, the surfactant system of this invention and the xylitol of this invention help suspend the nanoparticles.

The soluble calcium salt of this invention immediately replaces calcium lost to decay and food acids. Depending on the anion used, said calcium salt can also inhibit plaque bacteria and other mouth pathogens, and help preserve the products of this invention. Preferred antimicrobial anions include acetate and propionate.

The lactoferrin of this invention inhibits plaque bacteria and other mouth pathogens, and helps preserve the products of this invention. Preservative efficiency testing has shown that a mixture of lactoferrin (0.01 to 0.1% by weight) and calcium propionate (0.1 to 1.0% by weight) acts synergistically to preserve the dental products of this invention and inhibit plaque bacteria and other mouth pathogens.

One embodiment of this invention is a dentifrice comprising the mandatory ingredients, plus one or more optional ingredients, including an abrasive, water, and a mild flavor.

One embodiment of this invention is a low abrasivity prophylaxis paste comprising the mandatory ingredients, plus one or more optional ingredients, including an abrasive, water, and a mild flavor. Said prophylaxis paste will relieve dentinal hypersensitivity in the dental office and for weeks thereafter. And it does not splatter in use, unlike the conventional, stiff prophylaxis pastes. Another advantage is that the prophylaxis paste of this invention removes surface stain, plaque, and tartar, while leaving enamel intact.

One embodiment of this invention is a dental chewing gum comprising the mandatory ingredients, plus a mild flavor, plus 5 to 60% by weight of a gumbase selected from the group consisting of chicle and polybutenes.

One embodiment of this invention is a dentifrice powder comprising the mandatory ingredients, plus one or more optional ingredients, including an abrasive, and a mild flavor. If desired, the powder can be granulated by the usual methods. If further desired, the granules can be blended with 0.1 to 0.5% by weight of a tablet lubricant selected from the group consisting of calcium stearate, magnesium stearate, hydrogenated vegetable oil, and beeswax. The granules can be compressed into a tablet which disintegrates in the mouth and can then be chewed into a paste.

One embodiment of this invention is a toothpaste for infants and toddlers. Current products in this class suffer from a number of problems. Some have fluoride, which should not be swallowed. Some have silicones, and silica—inadvisable to swallow. Some have sufficient glycyrrhizin to cause hypokalemia. Most do not have xylitol—an excellent plaque suppressor. Some have large amounts of calcium phosphate and/or calcium carbonate which, when swallowed, can contribute significantly to the daily calcium dose for infants and toddlers. Some toothpastes for infants and toddlers have harsh detergents, such as SLS and cocamidopropyl betaine, which young children hate to taste.

A toothpaste for infants or toddlers should be ingestible without harm, providing only a minor contribution to their daily calcium requirement. Such a product, according to this invention, has a total calcium content of 5 to 10% by weight. Said formulation is excellent at healing or preventing caries, and it can be left in the mouth after brushing, without rinsing, to further reduce the opportunity for caries to occur.

One embodiment of this invention is a dental lozenge which can be sucked on by the user to treat and prevent caries, periodontal disease, halitosis, tooth sensitivity, and the other maladies addressed by the products of this invention.

One embodiment of this invention is a mouthwash which can be swished in the mouth and gargled before expectorating, to treat and prevent caries, periodontal disease, halitosis, tooth sensitivity, and the other maladies addressed by the products of this invention.

One embodiment of this invention is a dry mouth paste which can be placed in the mouth and applied all over the mouth, and swallowed whenever the user wishes. Said dry mouth paste is intended to ameliorate the condition of those who suffer from dry mouth by reducing irritation, and helping to keep the mouth moist. The total nanocalcite content of said dry mouth paste is 5 to 10% by weight. Said paste will treat and prevent caries, periodontal disease, halitosis, tooth sensitivity, and the other maladies addressed by the products of this invention.

A squib of this dry mouth paste can be placed in the mouth of a patient suffering from xerostomia, immediately before they go to sleep, in order to provide maximum protection against caries, gum disease, and oral candida infection while they sleep.

A squib of this dry mouth paste can be placed in the mouth of a patient suffering from xerostomia once every 2 hours throughout the day, in order to provide maximum protection against caries, gum disease, and oral candida infection.

The following are nonlimiting examples of the products and methods of this invention. All examples have been tested on humans, and have been found to be effective in relieving dentinal hypersensitivity, healing incipient caries or preventing caries, reducing or preventing plaque and tartar, preventing or treating periodontal disease and oral candida, halitosis, aphthous ulcers, oral mucositis, perioral dermatitis, and chapped lips, and ameliorating the condition of those who suffer from xerostomia and cold sores.

EXAMPLE 1

Dentifrice Powder, Granules, or Disintegrable Tablets

One of the embodiments of this invention is a dentifrice powder or granules. A typical formula for a dentifrice powder or granules according to the claims of this invention is:

| Ingredient | Weight % |
|---|---|
| nanosized CaCO$_3$ (Multifex MM) | 30.0 |
| xylitol | 51.0 |
| microcrystalline cellulose | 15.0 |
| Pluronic F127 | 2.0 |
| xanthan gum | 1.0 |
| Methocel K15M | 0.5 |
| flavor | 0.5 |

If desired, the granules can be blended with 0.5% by weight of a tablet lubricant and compressed into a tablet which disintegrates in the mouth and can then be chewed into a paste.

EXAMPLE 2

Dentifrice/Prophylaxis Paste

One of the embodiments of this invention is a dentifrice. A typical formula for a dentifrice according to the claims of this invention is:

| Ingredient | Weight % |
|---|---|
| xylitol | 36.0 |
| water | 32.0 |
| nanosized CaCO$_3$ (Multifex MM) | 10.0 |
| abrasive CaCO$_3$ (CalEssence 1500) | 5.0 |
| glycerin | 10.1 |
| Pluronic F127 | 4.0 |

-continued

| Ingredient | Weight % |
| --- | --- |
| cellulose gum (Aqualon 7MF) | 1.4 |
| Methocel K15M | 0.5 |
| flavor | 1.0 |

This dentifrice can also be used as a low abrasivity prophylaxis paste.

EXAMPLE 3

Toothpaste for Infants and Toddlers

A typical formula for an ingestible toothpaste according to the claims of this invention is:

| Ingredient | Weight % |
| --- | --- |
| xylitol | 36.0 |
| water | 30.0 |
| nanosized $CaCO_3$ (Multifex MM) | 5.0 |
| glycerin | 22.1 |
| Pluronic F127 | 4.0 |
| cellulose gum (Aqualon 7MF) | 1.4 |
| Methocel K15M | 0.5 |
| flavor | 1.0 |

EXAMPLE 4

Dental Lozenge

One of the embodiments of this invention is a dental lozenge. A typical formula for a lozenge according to the claims of this invention is:

| Ingredient | Weight % |
| --- | --- |
| xylitol | 90.0 |
| nanosized $CaCO_3$ (Multifex MM) | 6.0 |
| Pluronic F127 | 2.0 |
| cellulose gum (Aqualon 7MF) | 1.0 |
| Methocel K15M | 0.5 |
| flavor | 0.5 |

EXAMPLE 5

Dental Chewing Gum

One of the embodiments of this invention is a dental chewing gum. A typical formula for a chewing gum according to the claims of this invention is:

| Ingredient | Weight % |
| --- | --- |
| xylitol | 70.0 |
| gum base | 20.0 |
| nanosized $CaCO_3$ (Multifex MM) | 5.0 |
| Pluronic F127 | 2.0 |
| cellulose gum (Aqualon 7MF) | 1.0 |
| Methocel K15M | 0.5 |
| flavor | 1.5 |

EXAMPLE 6

Mouthwash

One of the embodiments of this invention is a mouthwash. A typical formula for a mouthwash according to the claims of this invention is:

| Ingredient | Weight % |
| --- | --- |
| water | 47.0 |
| xylitol | 36.0 |
| nanosized $CaCO_3$ (Multifex MM) | 5.0 |
| glycerin | 9.2 |
| Pluronic F127 | 1.6 |
| flavor | 0.5 |
| preservative | 0.4 |
| cellulose gum (Aqualon 7MF) | 0.2 |
| Methocel K15M | 0.1 |

EXAMPLE 7

Method for Eliminating Halitosis ("Morning Breath")

TOOTH BUILDER® Toothpaste is a product of SQUIGLE, inc, formulated according to the claims of this invention. It first appeared on the market in March, 2009.

Before you retire, floss, then brush your teeth with TOOTH BUILDER®. Gently brush your tongue, the roof of your mouth, and your cheeks. Rinse. Then place a new squib of TOOTH BUILDER® in your mouth and spread it around, especially on your tongue. Do not expectorate, but you may swallow. Go to sleep and, when you awake, your breath will be fresh and clean.

EXAMPLE 8

Dry Mouth Paste and Method of Use

One of the embodiments of this invention is a paste to ameliorate the oral health problems of those with xerostomia. A typical dry mouth paste, according to the claims of this invention is:

| Ingredient | Weight % |
| --- | --- |
| xylitol | 36.0 |
| water | 32.0 |
| nanosized $CaCO_3$ (Multifex MM) | 10.0 |
| glycerin | 15.1 |
| Pluronic F127 | 4.0 |
| cellulose gum (Aqualon 7MF) | 1.4 |
| Methocel K15M | 0.5 |
| flavor | 1.0 |

A squib of this dry mouth paste can be placed in the mouth of a patient suffering from xerostomia once every 2 hours throughout the day, in order to provide maximum protection against caries, gum disease, and oral candida infection.

A squib of this dry mouth paste can be placed in the mouth of a patient suffering from xerostomia, immediately before they go to sleep, in order to provide maximum protection against caries, gum disease, and oral candida infection while they sleep.

EXAMPLE 9

Method for Preventing and Treating Irritative Diseases in and Around the Mouth Aphthous ulcers (canker sores, mouth ulcers), perioral dermatitis and chapped lips are mainly due to harsh ingredients in oral care products causing irritation in people with sensitive skin in the mouth, lips, and the skin surrounding the mouth. These problems are best treated by:

a. Avoiding irritating oral care products, cosmetics, and foods
b. Flossing or using an irrigator
c. Using the oral care products of this invention

EXAMPLE 10

Method for Preventing and Treating Oral Mucositis

Oral mucositis is a condition that occurs when cancer patients are given certain chemotherapeutic agents, which interfere with the normal growth and reproduction of the skin inside the mouth. This situation predisposes said patients to ulceration at the slightest provocation, such as the use of conventional oral care products which contain many irritating ingredients. This problem is best treated and prevented by:

a. Avoiding irritating oral care products, cosmetics, and foods
b. Avoiding ingestion of sugars and alcoholic beverages
c. Flossing or using an irrigator
d. Getting enough sleep
e. Using the oral care products of this invention

EXAMPLE 11

Method for Preventing and Treating Cold Sores

Cold sores are an oral disease caused by a herpes virus which can infect the lips, tongue, and oral mucosa. Most of the time, the virus is in its latent state, and the patient is asymptomatic. But irritation and stress can trigger a reemergence of the virus. One of the triggers is the use of conventional oral care products, which contain many irritating ingredients. Although they cannot currently be cured (permanently eradicated), cold sores can be reduced in frequency, and outbreaks can be ameliorated by:

a. Avoiding irritating oral care products, cosmetics, foods, and excessive sunlight
b. Flossing or using an irrigator
c. Using the oral care products of this invention

EXAMPLE 12

Method for Preventing and Treating Oral Candida (Thrush)

The fungus *candida albicans* is an indigenous inhabitant of many body orifices, including the mouth and throat. Normally, it does no harm, but if an overgrowth occurs, symptoms appear, including pain, and eventually oral cancer, if a rampant infection persists for years. A properly tuned immune system can keep candida in check. But irritation and stress can trigger an overgrowth, and recurrence of symptoms in susceptible individuals. One of the triggers is the use of conventional oral care products, which contain many irritating ingredients. Although candida cannot be permanently eradicated, it can be held in check by:

a. Avoiding irritating oral care products, cosmetics, and foods,
b. Avoiding ingestion of sugars and alcoholic beverages
c. Flossing or using an irrigator
d. Using the oral care products of this invention

I claim:

1. Dental products to prevent and treat dentinal hypersensitivity, prevent tooth decay and heal incipient caries, prevent formation of oral plaque and tartar, prevent and treat aphthous ulcers, oral mucositis, periodontal disease, perioral dermatitis, halitosis, oral candida, and chapped lips, and ameliorate the condition of those suffering from xerostomia and cold sores, comprising:

(a) 0.25 to 40 weight percent of nanocalcite particles having a particle size of 1 to 1000 nm;
   (b) 8 to 95% by weight of xylitol;
   (c) a surfactant system employing poloxamer as the main surfactant, wherein said poloxamer, or a mixture of poloxamers, comprise 0.01 to 10 weight % of said dental product, said system further comprising anionic polysaccharide (AP), or a mixture of APs, plus a nonionic cellulose ether (NCE), or a mixture of NCEs, in a ternary surfactant system having enhanced foaming power relative to poloxamers alone or to poloxamers plus APs or to poloxamers plus NCEs, wherein the weight ratio of said poloxamer to said APs is greater than 1, and the weight ratio of said AP to said NCE is greater than 1;
   (d) said dental products being essentially free of all surfactants other than those in the ternary surfactant system of poloxamers, APs, and NCEs;
   (e) said dental products being free of irritating detergents, said detergents including sodium lauryl sulfate, sodium N-lauroyl sarcosinate, cocamidopropyl betaine, sodium N-lauroyl glutamate, and sodium methyl cocoyl taurate;
   (f) said dental products being free of irritating flavors and essential oils, said flavors and oils including phenol, thymol, carvacrol, clove, spearmint, cinnamon, eucalyptol, and any flavors present at high intensity;
   (g) said dental products being free of irritating antimicrobials, said antimicrobials including chlorhexidine, alexidine, cetylpyridinium chloride, benzalkonium chloride, benzethonium chloride, sanguinarine, and triclosan;
   (h) said dental products being free of irritating tartar control agents, said agents including inorganic phosphate salts of group I metals, including metaphosphates, polyphosphates, and pyrophosphates;
   (i) said dental products being free of foam suppressors, said suppressors including sulfonated polyacrylate oligomers, polydimethylsiloxanes, and azacycloalkane-2,2-diphosphonic acids.

2. A dental product according to claim 1, wherein the poloxamer consists of a block copolymer of ethylene oxide and propylene oxide arranged as $(EO)_a(PO)_b(EO)_a$ wherein the PO content ranges from 15 to 85 mole percent, and the molecular weight ranges from 1,000 to 30,000.

3. A dental product according to claim 1, wherein said anionic polysaccharides are selected from the group consisting of alginic acid, gum arabic, carrageenan, carboxymethyl cellulose, karaya gum, pectin, gum tragacanth, and xanthan gum.

4. A dental product according to claim 1, wherein the nonionic cellulose ether is selected from the group consisting of alkylated celluloses and hydroxyalkylated celluloses.

5. A dental product according to claim 1, further comprising one or more optional ingredients:
   (a) 5 to 90% by weight of polyol humectants selected from the group consisting of glycerol, erythritol, sorbitol, mannitol, maltitol, and polyethylene glycol;
   (b) 0.001 to 5% by weight of sweeteners selected from the group consisting of acesulfame and its salts, aspartame, dihydrochalcones, glycyrrhizin and its derivatives, raw and extracted licorice, saccharin, stevia and the rebaudosides, sucralose, talin and the thaumatins;
   (c) 1 to 60% by weight of a mild abrasive, having a hardness less than or equal to that of tooth enamel, selected from the group consisting of calcium carbonate, dibasic calcium phosphate, tribasic calcium phosphate, calcium pyrophosphate, and hydroxyapatite;
   (d) 1 to 60% by weight of a strong abrasive, having a hardness greater than that of tooth enamel, selected from the group consisting of alumina, silica, titania, and fluoroapatite;
   (e) 0.1 to 10% by weight of flavor;
   (f) 1 to 5000 ppm by weight of a fluoride containing compound selected from the group consisting of sodium fluoride and sodium monofluorophosphate;
   (g) 0.1 to 10% by weight of a mono-, di-, or polydentate acid or its salts selected from the group consisting of citric acid, ethylenediaminetetraacetic acid, ascorbic acid, phosphoric acid, hydrochloric acid, and sulfuric acid to adjust and maintain the pH between 6 and 10;
   (h) 0.1 to 1.0% by weight of preservative selected from the group consisting of paraben, potassium sorbate, lactoferrin, lysozyme, and calcium propionate;
   (i) 0.1 to 1.0% by weight of antioxidant selected from the group consisting of ascorbic acid, α-tocopherol, β-carotene, coenzyme $Q_{10}$ and melatonin;
   (j) 5 to 95% by weight of water; or
   (k) 0.1 to 10% of a thickener selected from the group consisting of colloidal cellulose, hydrated silica, polyethylene glycol, and polyvinylpyrrolidone.

6. A dental product according to claim 5, wherein lactoferrin and calcium propionate are present in sufficient quantities to synergistically preserve said dental product and inhibit plaque bacteria and other mouth pathogens.

7. A dental product according to claim 1, wherein high molecular weight polyethylene oxides (PEOs) fully or partially replace the nonionic cellulose ethers; and said PEOs have a molecular weight range of 100,000 to 8 million.

8. A dental product according to claim 1, wherein high molecular weight polyacrylic acids (PAAs), linear or crosslinked, fully or partially replace the anionic polysaccharides; and said PAAs have a molecular weight range of 700,000 to 5 million.

9. A dental product according to claim 5, in the form of a chewing gum, said dental product further comprising 5 to 60% by weight of a gumbase selected from the group consisting of chicle and polybutenes.

10. A dental product according to claim 5, in the form of a dentifrice powder, said dental product further comprising one or more optional ingredients, including an abrasive, and a mild flavor; if desired, the powder can be granulated by the usual methods; if further desired, the granules can be blended with 0.1 to 0.5% by weight of a tablet lubricant selected from the group consisting of calcium stearate, magnesium stearate, hydrogenated vegetable oil, and beeswax; the granules can be compressed into a tablet which disintegrates in the mouth and can then be chewed into a paste.

11. A dental product according to claim 5 in the form of a toothpaste for infants and toddlers, wherein the total calcium content of said toothpaste is 5 to 10% by weight.

12. A dental product according to claim 5 in the form of a toothpaste, which removes surface stain, plaque, and tartar, while leaving tooth enamel intact, and decreasing or eliminating tooth sensitivity over a period of 7 to 14 days; said toothpaste also prevents tooth decay and heals incipient caries.

13. A dental product according to claim 5 in the form of a low abrasivity prophylaxis paste, which removes surface stain, plaque, and tartar, while leaving tooth enamel intact; and it relieves dentinal hypersensitivity in the dental office, and for weeks thereafter.

14. A dental product according to claim 5 in the form of a dry mouth paste to ameliorate the oral problems of people suffering from xerostomia, including caries, periodontal disease, oral candida, and halitosis, wherein the nanocalcite content of said dry mouth paste is 5 to 10% by weight.

15. A dental product according to claim 5 in the form of a lozenge, which decreases or eliminates tooth sensitivity while satisfying the user's desire for a pleasant confection; said lozenge also prevents tooth decay and heals incipient caries.

16. A dental product according to claim 5 in the form of a mouthwash, which decreases or eliminates tooth sensitivity while treating and preventing halitosis; said mouthwash also prevents tooth decay and heals incipient caries.

17. A method to treat and prevent halitosis wherein an individual, prior to retiring, flosses, then brushes his teeth with the dentifrice according to claim 5; gently brushing the tongue, roof of the mouth, and cheeks; rinsing, then placing a new squib of the dentifrice in his mouth and spreading it around, especially on the tongue; not expectorating, but swallowing as needed; going to sleep; and upon awakening, his breath will be fresh and clean.

18. A method to ameliorate the oral health problems associated with xerostomia, comprising: place a squib of the dry mouth paste according to claim 14 in the mouth of a patient suffering from xerostomia, immediately before they go to sleep, in order to provide maximum protection against caries, gum disease, oral candida, and halitosis while they sleep; and where a squib of this formulation can also be placed in the patient's mouth once every 2 hours throughout the day.

19. A method of preventing or treating cold sores, comprising:
   (a) avoiding irritating oral care products, cosmetics, foods, and excessive sunlight;
   (b) flossing or using an irrigator;
   (c) getting enough sleep; and
   (d) using oral care products of claim 5.

20. A method of preventing or treating oral candida (thrush), comprising:
   (a) avoiding irritating oral care products, cosmetics, and foods;
   (b) avoiding ingestion of sugars and alcoholic beverages;
   (c) flossing or using an irrigator;
   (d) getting enough sleep; and
   (e) using oral care products of claim 5.

21. A method of preventing or treating oral mucositis, comprising:
   (a) avoiding irritating oral care products, cosmetics, and foods;
   (b) avoiding ingestion of sugars and alcoholic beverages;
   (c) flossing or using an irrigator;
   (d) getting enough sleep; and
   (e) using oral care products of claim 5.

22. A method of preventing or treating aphthous ulcers, perioral dermatitis, and chapped lips, comprising:
  (a) avoiding irritating oral care products, cosmetics, and foods;
  (b) flossing or using an irrigator; and
  (c) using oral care products of claim 5.

23. A dental product according to claim 4, wherein the alkylated celluloses and hydroxyalkylated celluloses are selected from the group consisting of methylcellulose, ethyl cellulose, hydroxyethyl cellulose, hydroxypropyl cellulose, and hydroxypropyl methylcellulose.

* * * * *